United States Patent [19]

Korcek et al.

[11] Patent Number: 4,745,070

[45] Date of Patent: May 17, 1988

[54] METHOD FOR ASSESSMENT OF HIGH TEMPERATURE ANTIOXIDANT CAPABILITIES OF ENGINE OILS, BASE OILS & ENGINE OIL ADDITIVES

[75] Inventors: Stefan Korcek, Birmingham; Milton D. Johnson, Livonia, both of Mich.

[73] Assignee: Ford Motor Company, Dearborn, Mich.

[21] Appl. No.: 28,057

[22] Filed: Mar. 19, 1987

Related U.S. Application Data

[63] Continuation of Ser. No. 725,609, Apr. 22, 1985, abandoned.

[51] Int. Cl.$^4$ ............................................. G01N 33/28
[52] U.S. Cl. .................................. 436/60; 436/85; 436/155
[58] Field of Search ..................... 436/60, 61, 85, 155

[56] References Cited

U.S. PATENT DOCUMENTS 4,155,713  5/1979  Mahoney ............................. 436/60
4,438,203  3/1984  Wohltjen et al. ..................... 436/60

FOREIGN PATENT DOCUMENTS 648905  2/1979  U.S.S.R. ................................ 436/60

OTHER PUBLICATIONS

The Effect of Fuel Combustion Products on Antioxidant Consumption in a Synthetic Engine Oil, L. R. Mahoney, K. Otto, S. Korcek, and M. D. Johnson, Ind. Eng. Chem. Prod. Res. Dev., 19, 11–15, (1980).

Inhibition of Oxidation by ZDTP and Ashless Antioxidants in the Presence of Hydroperoxides at 160° C.--Part 1, M. D. Johnson, S. Korcek, and M. Zinbo, SAE Technical Paper 831684, 1983.

Oxidation Characteristics of Inhibited Mineral Oils, ASTM Standard Test Method D943.

Oxidation Stability of Steam Turbine Oils by Rotating Bomb, ASTM Standard Test Method D2272.

Evaluation of Automotive Crankcase Lubricants by Differential Scanning Calorimetry, S. M. Hsu, A. L. Cummings, and D. B. Clark, SAE Technical Paper 821252, 1982.

A Thin–Film Oxygen Uptake Test for the Evaluation of Automotive Crankcase Lubricants, C. Ku and S. M. Hsu Lubrication Engineering, 40(2), 75–83 (1984).

Polymer Handbook, 2nd edition, edited by J. Brandrup and E. H. Immergut, J. Wiley and Sons, 1975, pp. II–1 et seq.

Liquid–Phase Autoxidation of Organic Compounds at Elevated Temperatures, 1. The Stirred Flow Reactor Technique and Analysis of Primary Products from n–Hexadecane Autoxidation at 120°–180° C., R. K. Jensen, S. Korcek, L. R. Mahoney, and M. Zinbo, J. Am. Chem. Soc. 101, 7574 (1979).

Kinetics and Mechanisms of the Autoxidation of Pentaerythrityl Tetraheptanoate at 180°–220° C., E. J. Hamilton, Jr., S. Koreck, L. R. Mahoney and M. Zinbo, Int. J. Chem. Kinet., 12 577 (1980).

Primary Examiner—Michael S. Marcus
Attorney, Agent, or Firm—Lorraine S. Melotik; Roger L. May

[57] ABSTRACT

This invention relates to a method for assessing the high temperature antioxidant capabilities of engine oils, base oils and engine oil additives under oxidative conditions simulating those encountered in an operating internal combustion engine. In particular, the method of this invention evaluates the above materials under conditions of a continuous influx of free radicals or materials capable of breaking down into free radicals and at elevated temperatures, i.e., similar to engine oil operational temperatures.

19 Claims, 3 Drawing Sheets

METHOD FOR ASSESSMENT OF HIGH TEMPERATURE ANTIOXIDANT CAPABILITIES OF ENGINE OILS, BASE OILS & ENGINE OIL ADDITIVES

This application is a continuation now abandon of application Ser. No. 725,609, filed 04/22/85.

Technical Field

This invention relates to a method for assessing the high temperature antioxidant capabilities of engine oils, base oils and engine oil additives under oxidative conditions simulating conditions encountered in an operating internal combustion engine.

BACKGROUND OF THE INVENTION

Oxidation is the most important process leading to engine oil degradation in internal combustion engines. The oil oxidation takes place primarily in the piston-cylinder area of the engine wherein a thin film of oil is subjected to high temperatures, high shear stress and combustion products. As a result, oil viscosity increases and acidic products, insolubles, sludge and varnish are formed. We have proposed a model for the oxidation of engine oils as it occurs in operating internal combustion engines in "Inhibition of Oxidation by ZDTP and Ashless Antioxidants in the Presence of Hydroperoxides at 160° C.—Part I", M. D. Johnson, S. Korcek, M. Zinbo, SAE Technical Paper No. 831684 (1984), which is shown in FIG. 1. According to this model, the oxidation of engine oil is initiated by free radicals which are continuously produced during the combustion process or, additionally, may be derived from the decomposition of primary oxidation products, such as hydroperoxides, ROOH. These free radicals may react with the oil, RH, and, in the presence of oxygen, form peroxy radicals, $RO_2\cdot$. In the absence of antioxidants, peroxy radicals can further react with additional oil to form hydroperoxides and alkyl radicals, $R\cdot$. This continues in a chain reaction process which can result in the formation of a high concentration of hydroperoxides. The chain reaction process can be inhibited by adding radical trapping antioxidants, AH, to the oil. In that case, peroxy radicals react preferentially with the radical trapping antioxidant to give non-radical products and keep the hydroperoxide concentration low. Formation of hydroperoxides is accompanied by radical formation from thermal and/or catalytic decomposition of the hydroperoxides which accelerates the oxidation. This initiation process can be prevented by the addition of peroxide decomposing antioxidants which convert hydroperoxides into non-radical products. Thus, to protect the oil against oxidative degradation in service, both types of antioxidants, radical trapping and peroxide decomposing, are used in engine oil formulations. Hindered phenols and amines are typical representatives of the first type of antioxidants, while zinc dialkylthiophosphates, ZDTP, are believed to react by both mechanisms. In some engine oils, ZDTP are the only antioxidants used, while in other oils they are supplemented by other antioxidants, such as amines and hindered phenols. In addition to the synthetic antioxidants added to the oil, engine oils may also contain "natural inhibitors" depending on the crude oil source and the method and degree of refining. Nevertheless, the majority of protection is provided by synthetic antioxidant additives. Determination of the antioxidant capability of engine oils is one of the most important technological parameters characterizing the oxidation properties of new oils and the remaining useful life of used oils.

Based on the above model for the oxidation of oils in internal combustion engines, it can be seen that hydroperoxide products are continuously formed in engine oils during engine operation due to a continuous influx of free radicals from the combustion process, even in the case when oxidation is inhibited by free radical trapping antioxidants. Since hydroperoxides at elevated temperatures initiate and accelerate further oxidation, their decomposition by peroxide decomposing antioxidants is not only a very important inhibition process but also an important process of antioxidant consumption. Therefore, in order to simulate oxidative conditions encountered in operating engines, the antioxidant capability of engine oils, base oils, and engine oil additives should be evaluated at elevated temperatures and under conditions of a continuous influx of free radicals or materials capable of breaking down into free radicals, e.g., peroxidic compounds.

Conventional laboratory tests currently used for the evaluation of antioxidant capabilities of engine oils, base oils and engine oil additives consist of determination of an inhibition period afforded by antioxidant species present in these materials. The inhibition period is determined from measurements of oxygen absorption (e.g., in an oxidation bomb apparatus), heat of reaction (e.g., DSC), formation of reaction products (e.g., acids, peroxides, insolubles, gaseous products), and/or change in physico-chemical properties (e.g., increase of viscosity). Exemplary of such tests are ASTM Standard Test Methods D943 and D2272 and that described in "Evaluation of Automotive Crankcase Lubricants by Differential Scanning Calorimetry", S.M. Hsu, A.L. Cummings, and D.B. Clark, SAE Technical Paper 821252, 1982. These tests are performed under various oxidative conditions at elevated temperatures (up to 160° C.). None of these tests, however, include any provision to simulate the continuous influx of free radicals into the test materials. In the early stages of testing, the initiation of oxidation in these tests occurs only by the direct reactions of oxygen with oil components and it is only in the latter stages that the formation of free radicals is accelerated due to the radical decomposition of the hydroperoxides formed.

In the paper entitled "A Thin-Film Oxygen Uptake Test For The Evaluation of Crankcase Lubricants", C. Ku and S.M. Hsu, Lubrication Engineering, 40(2), 75–83 (1984), an oxidation test method is described which includes the addition of oxidized fuel components as a catalyst of oxidation. This test involves addition of the oxidized fuel components prior to beginning the oxidation test and, therefore, does not simulate the continuous interaction of combustion derived free radical species with the oil, which results in the continuous formation of hydroperoxides.

Another type of test which is used for evaluation of antioxidant capacity of engine oils or determination of antioxidant concentration in various hydrocarbonaceous materials is described in U.S. Pat. No. 4,155,713 to Mahoney. This type of test comprises the determination of free radical trapping antioxidant capability by titration with peroxy radicals at low temperatures (usually 60° C.). This titration with peroxy radicals, simulates a continuous influx of free radicals, however, it can be performed only at reaction temperatures which are much lower than those encountered by oil in an operating engine. Under such test conditions, initiation of oxidation by the free radicals produced by the thermal decomposition of hydroperoxides is completely suppressed and interactions of antioxidants with hydroperoxides are partially suppressed.

Thus, currently used laboratory tests for evaluation of antioxidant capabilities of engine oils, base oils and engine oil additives do not simulate the oxidative conditions encountered in an operating internal combustion engine as described by our model.

BRIEF DESCRIPTION OF THE INVENTION

The invention of this application is directed to a method for assessing the high temperature antioxidant capabilities of materials, which are selected from engine oils, base oils, and engine oil additives and which comprise antioxidant species, under conditions simulating those encountered in an operating internal combustion engine. The method comprises (a) oxidizing the materials in a reactor by means of a gas comprising oxygen and at an elevated temperature, while concurrently and continuously introducing free radicals or materials capable of breaking down into free radicals into the reaction mixture, (b) monitoring the extent of oxidation of the reaction mixture and (c) determining the delay in the oxidative breakdown (inhibition period) of the reaction mixture attributable to the antioxidant species present in the reaction mixture. The materials to be assessed may be employed in solution in an oxidizable solvent.

DETAILED DESCRIPTION OF THE INVENTION

Figure 1:
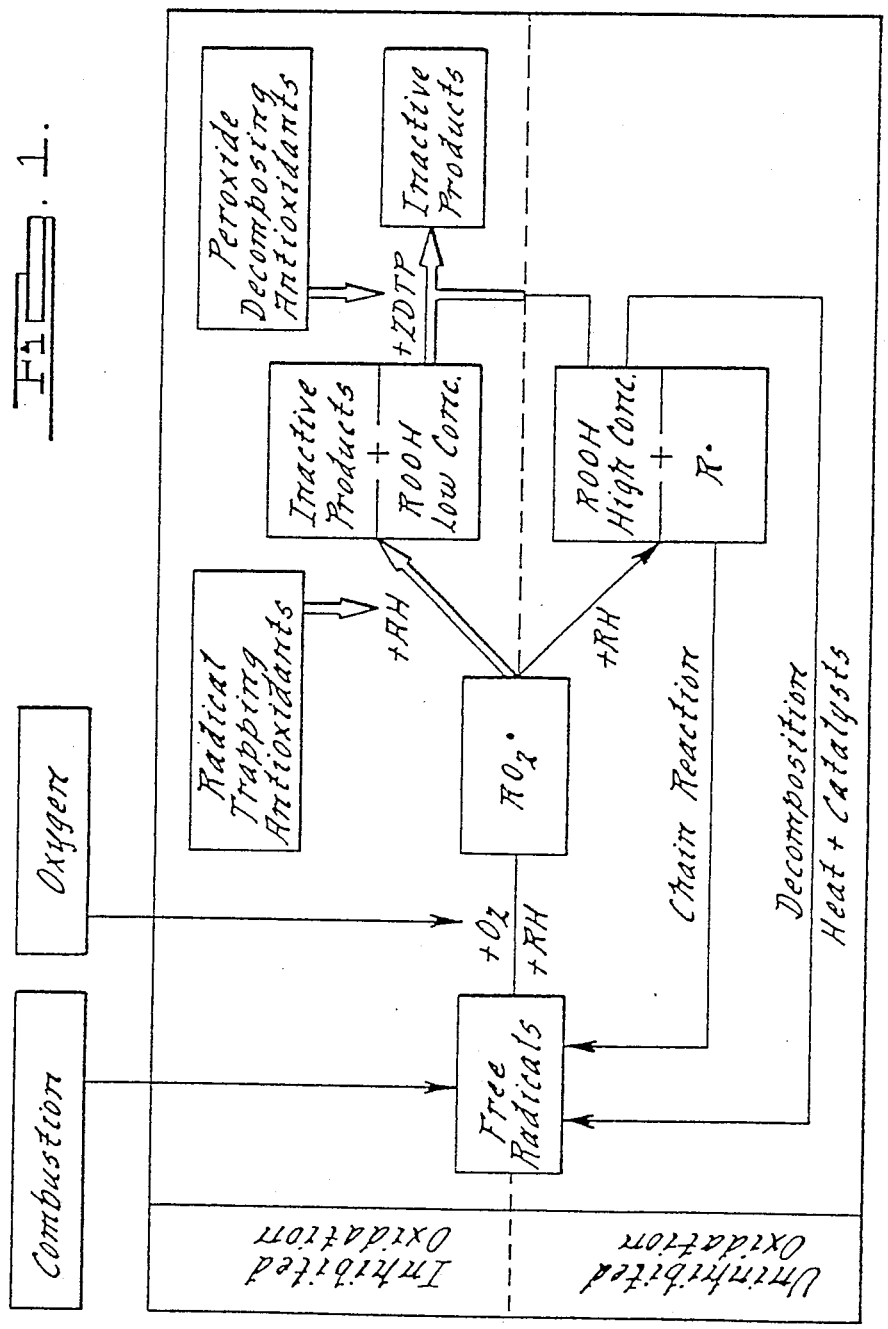
FIG. 1 is a diagram presenting a model for engine oil oxidation as it occurs in operating internal combustion engines. Processes of initiation, inhibited oxidation, and uninhibited oxidation are depicted.

The method of this invention, as disclosed above, relates to the model for the oxidation of oils in an operating internal combustion engine as described in the Background of the Invention (FIG. 1). The method of this invention evaluates the high temperature antioxidant capabilities for both the radical trapping and peroxide decomposing antioxidant species under conditions comprising the continuous influx of free radicals and the continuous formation of peroxidic compounds. This is achieved by oxidizing, at an elevated temperature, the materials to be evaluated (engine oils, base oils and engine oil additives) in a reactor by means of an oxidizing gas comprising oxygen, while continuously introducing free radicals or materials capable of breaking down into free radicals into the reaction mixture. If antioxidant species are present in the reaction mixture, the oxidation is inhibited until they are completely consumed by reactions with free radicals and peroxidic compounds. At that point, uninhibited oxidation begins. The delay before this uninhibited oxidation starts, at a given rate of introducing said radicals or materials capable of breaking down to form free radicals, is proportional to the level of antioxidant species present in the reaction mixture. By means of the method of this invention, assessment of high temperature antioxidant capability can be conducted using a variety of experimental apparatus, procedures, conditions, and reagents, selection of which would be within the skill of those in the art. The following general guidelines and examples for these selections are intended to assist in the use of this invention but are not meant to be limiting. Many modifications of such apparatus, procedures, etc., would be apparent to those in the art. Thus, other selections than those described below may be made as desired.

Initial Reaction System

The materials to be evaluated according to the method of this invention are selected from engine oils (new and used), base oils, and engine oil additives. Such materials are well known in the art and their selection would be within the skill of those in the art. The materials to be evaluated may be subjected to oxidation as such or as solutions in an oxidizable solvent. If desired, an oxidation catalyst may also be added into the materials or their solutions prior to the initiation of oxidation according to the method of this invention.

Oxidizable Solvent

The oxidizable solvent may be used to function not only as a diluent but also as a model oxidation system for detection of an oxidative breakdown (inhibition period). Important considerations in selection of a solvent are (a) low volatility under the test conditions employed, (b) sufficiently low viscosity to facilitate contact of reactants, (c) similarity and inertness to and compatibility with materials to be tested, and (d) sufficient oxidizability for convenient detection of an oxidative breakdown. Suitable oxidizable solvents include, for example, n-hexadecane for mineral oils, synthetic hydrocarbon oils, mineral base oils, and additives and pentaerythrityl tetraheptanoate for synthetic ester oils.

Oxidation Catalyst

An oxidation catalyst may be added into the materials to be assessed by the method of this invention, or their solutions, to accelerate the oxidation, for example, by catalytic decomposition of peroxidic compounds. The oxidation catalyst is added prior to the oxidation of the reaction mixture. Suitable catalysts, which could be used, for example, are metallic copper, copper naphthenates, and Standard Reference Material 1817 (A Catalyst Package for Lubricant Oxidation, available from the U.S. Dept. of Commerce, National Bureau of Standards).

Oxidizing Gas

The oxidizing gas comprises oxygen. In addition to oxygen, the oxidizing gas may comprise other gases, e.g., inert gases, free radical gases, hydrocarbons and water vapor. Exemplary of such mixtures, which may be employed as the oxidizing gas in this invention, are ambient air, and the gaseous combustion products produced in a pulse flame apparatus as described in "The Effect of Fuel Combustion Products on Antioxidant Consumption in a Synthetic Engine Oil", L.R. Mahoney, K. Otto, S. Korcek, and M.D. Johnson, Ind. Eng. Chem. Prod. Res. Dev., 19, 11–15 (1980). In this apparatus, engine fuels or model fuels comprising hydrocarbons, such as isooctane or cetane, are burned in oxygen to simulate combustion in an internal combustion engine. This gaseous combustion product contains oxygen, carbon monoxide, carbon dioxide and free radical nitrogen oxides. The oxidizing gas is introduced into the reactor and contacted with the reaction mixture, for example, by bubbling the oxidizing gas through the reaction mixture, flowing the oxidizing gas through the space above the reaction mixture while stirring the reaction mixture, or forcing the diffusion of the oxidizing gas into the reaction mixture by means of pressure. Selection of the rate of introduction of the oxidizing gas into the reaction mixture would be within the skill of those in the art.

Reaction Pressure

Determinations can be carried out at any suitable test pressure depending, for example, on reactor design, type of material tested and means of producing oxidizing gas. While generally it is most convenient to carry out the testing at ambient pressures, any suitable pressure may be used. Optimal pressure selection would be within the skill of one in the art.

Reaction Temperature

The method of this invention is carried out at an elevated temperature, i.e., similar to the temperatures encountered by the oil in operating internal combustion engines. This temperature may be, for example, representative of those in critical engine locations such as piston-cylinder areas or, alternatively, typical of that found in the crankcase or bearings. Generally, the test temperature should be in the range of 100°–200° C., however, such temperature range is not meant to be limiting to the method of this invention. In the testing described in the examples, a temperature of 160° C. was exemplarily used.

Free Radicals and Materials Capable of Breaking Down Into Free Radicals.

In order to simulate oxidative conditions encountered in an operating internal combustion engine, free radicals or materials capable of breaking down into free radicals are continuously introduced into the reaction mixture. Free radicals, which may be so employed, are introduced into the reaction mixture as a gas comprising gaseous free radicals. The gas which may be employed in this invention as a source of gaseous free radicals may comprise such gaseous free radicals as nitrogen oxides ($NO_x$·). This gas may also comprise other gases, e.g., inert gases or oxidizing gases, which would not interfere with the method of this invention. Such a gas which may be used in this invention is the gas mixture produced by combustion of hydrocarbon fuels in the pulse flame apparatus described above. The gas comprising gaseous free radicals may be added into the reaction mixture along with the stream of the oxidizing gas. However, since the combustion product gas mixture produced by the pulse flame apparatus contains both free radicals, (e.g., ·OH, R·, $NO_x$·) and oxygen, this combustion product gas may be singly employed as the source of the gaseous free radicals and the oxidizing gas.

Alternately, or in addition to introducing free radicals into the reaction mixture as described above, materials capable of breaking down into free radicals may be continuously introduced into the reaction mixture. Materials that are capable of breaking down into free radicals and that can be used herein are well known to those in the art. Various such materials, which can be employed in this invention are described, for example, in Polymer Handbook, 2nd Ed., edited by J.B. Brandrup and E.H. Immergut, J. Wiley and Sons, 1975, p II-1 et seq. Exemplary of such materials are peroxidic compounds (i.e., compounds containing the —O—O— moiety), azonitriles, and other azoderivatives. As is well known in the art, the rate at which such materials break down into free radicals varies, and is dependent, for example, on the temperature to which they are subjected. Some such materials would be labeled as good free radical initiators at the temperature of the method of this invention, i.e., they would break down rapidly into free radical at the temperature of the method of this invention. Exemplary of such materials are α-phenylethyl-azo-methane, azo-bis-isobutanoldiacetate and dicumylperoxide. Other such free radical initiator materials break down more slowly into free radicals; exemplary of such material are cumene hydroperoxide and tert-butyl hydroperoxide. Still other such materials (i.e., those which break down slowly) that may be employed in this invention are peroxidic compounds prepared, e.g., by oxidation of oxidizable materials (preferably of the same oxidizable solvents discussed above) by various means as is known in the art. For example, hexadecyl hydroperoxides may be produced by the oxidation of n-hexadecane in the stirred flow reactor, as taught in "Liquid-Phase Autoxidation of Organic Compounds at Elevated Temperatures. 1. The Stirred Flow Reactor Technique and Analysis of Primary Products from n-Hexadecane Autoxidation at 120–180° C.", R.K. Jensen, S. Korcek, L.R. Mahoney, and M. Zinbo, J. Am. Chem. Soc. 101, 7574 (1979). While various free radicals and materials capable of breaking down into free radicals have been described, their description is not meant to be limiting. Selection of other such suitable materials would be apparent to those in the art.

In this invention, the materials capable of breaking down into free radicals may be employed as is or in solution in a solvent. In those instances wherein such materials are a liquid, they may conveniently be employed as is or in a solvent solution. However, when they are in solid form they are preferably employed in a solvent solution. The solvent may be an oxidizable solvent, such as those described above. Selection of the rate of addition of the free radical materials capable of breaking down into free radicals to the reaction mixture is not critical to the method of this invention and selection of such would be within the skill of those in the art.

Reactor

Various reactors are suitable for use in the method of this invention. The choice of the optimal reactor to be employed would depend upon the selection of the particular embodiment of the method which is employed. Exemplary of reactors which could be used for this purpose are: (a) a batch reactor, with the continuous bubbling of oxidizing gas through the reaction mixture and provisions for the continuous addition of a solution of free radical initiators, the continuous measurement of temperature, and periodic withdrawal of samples of the reaction mixture for analyses, (b) a stirred flow reactor, referenced above, with provisions for the continuous introduction of a solution of peroxidic compounds in an oxidizable solvent with the stream of oxidizing gas and the continuous withdrawal of the reaction mixture, (c) a batch reactor suitable for the continuous introduction of the combustion products produced in a combustion device such as a pulse flame generator, which combustion products, as described above, contain free radicals and an oxidizing gas. Other embodiments of reactions may be employed in the method of this invention, their selection is not to be construed as limited to those described above.

Monitoring Extent of Oxidation

The extent of oxidation can be monitored using various techniques and methods either continuously or periodically. These techniques and methods include, but are not limited to, monitoring such parameters as measurement of oxygen absorption, measurement of reaction temperature, measurement of IR absorption, determination of total oxidation products or individual oxidation products such as hydroperoxides, acids, gaseous products, etc., and measurement of change of physicochemical properties such as viscosity, etc.

Detection of Oxidative Breakdown

Oxidative breakdown can be detected from a sudden change in the selected monitoring parameter. For example, a very convenient way to accomplish this is by measuring the temperature change directly in the reaction system. Upon consumption of antioxidants, the temperature increases since the oxidation reactions are exothermic.

Measure of Antioxidant Capability

The antioxidant capability at given test conditions can be expressed, e.g., by the time to reach oxidative breakdown (inhibition time), or by the amount of free radicals (e.g., as based on free radical producing species such as peroxidic compounds) required to be added to reach oxidative breakdown per unit mass, volume, or amount (moles) of tested material.

The invention will be further understood by referring to the following detailed examples which are presented by way of illustration and not by way of limitation.

EXAMPLE 1

Antioxidant Capability of New Engine Oils

Antioxidant capabilities of new engine oils were experimentally determined by (a) oxidizing a solution of engine oil in n-hexadecane with pure oxygen gas at 160° C. and atmospheric pressure while continuously introducing a solution of peroxidic compounds obtained by oxidation of n-hexadecane, (b) monitoring reaction temperature and hydroperoxide concentration in the reaction mixture, (c) detecting the delay in oxidative breakdown of the reaction mixture from the first increase of the temperature and from the delay of uninhibited formation of hydroperoxides.

Materials Assessed

Oil A—Mineral engine oil (10W40, SE/CC) containing ZDTP antioxidant additive.

Oil B—Synthetic hydrocarbon engine oil (5W20, SF/CC) containing ZDTP and ashless radical trapping antioxidants.

Reagents (1) n-hexadecane (99+%) from Aldrich Chemical Company was purified to remove polar impurities using silica gel and alumina (for procedure see the above referenced J. Am. Chem. Soc. 101, 7574 (1979)).

(2) Argon was Matheson Grade (min. purity 99.9995%).

(3) Oxygen was Matheson UHP (min. purity 99.99%).

(4) The solution of peroxidic compounds was prepared by oxidation of n-hexadecane using oxygen gas in the stirred flow reactor at 160° C. and 110 kPa with the residence time of 400 s (for detailed procedure and apparatus see the above reference). The concentration of hydroperoxides, [—OOH], in the peroxidic solution was 13.7 mM.

Analytical Procedures

The concentration of hydroperoxides in the solution of peroxidic compounds or in the reaction mixture was determined using an iodometric procedure which is described in the above reference in J. Am. Chem. Sec. 101, 7574 (1979).

Apparatus

Determination of antioxidant capability was performed in a flow reactor system which consisted of a Pyrex glass reactor similar to a batch reactor described in "Kinetics and Mechanisms of the Autoxidation of Pentaerythrityl Tetraheptanoate at 180–220° C.", E.J. Hamilton, Jr., S. Korcek, L.R. Mahoney and M. Zinbo, Int. J. Chem. Kinet., 12, 577 (1980). Provisions for continuous introduction of the solution of peroxidic compounds were made and samples were withdrawn periodically. The reactor was used with the same oxygen and argon supply system and constant temperature bath as those described in the above referenced J. Am. Chem. Soc. 101, 7574 (1979). The solution of peroxidic compounds was introduced using a syringe pump (Chromatronix Cheminert Metering Pump CMP-3V). Samples of reaction mixture were withdrawn using disposable pipets. The temperature in the reactor was measured continuously using a glass-shielded Chromel-Alumel thermocouple.

Procedure

The reactor was placed in a 160° C. constant temperature bath and flushed with argon. n-Hexadecane (37.6 mL) was added into the reactor and then heated to reaction temperature of 160° C. under a continuous flow of argon for 700 s. At 40 s before the beginning of the test a 2.4 mL sample of the test oil was added into the reactor. The flow of oxygen was switched on at a time (20 s before the beginning of the test) such that it reached the reaction mixture at the beginning of the test. Oxygen gas, preheated to the reaction temperature, was bubbled throughout the reaction mixture at the rate of 3.3 mL/s (at standard conditions) during the entire test. Introduction of the peroxidic solution began at 100 s at the rate of 0.01 mL/s. At 50 s, 300 s, and thereafter at 200 s intervals, 2 mL samples of reaction mixture were withdrawn, chilled, and subsequently analyzed. The temperature reading was taken every 200 s. The test was discontinued after a substantial increase in temperature was observed.

Results

Figure 2:
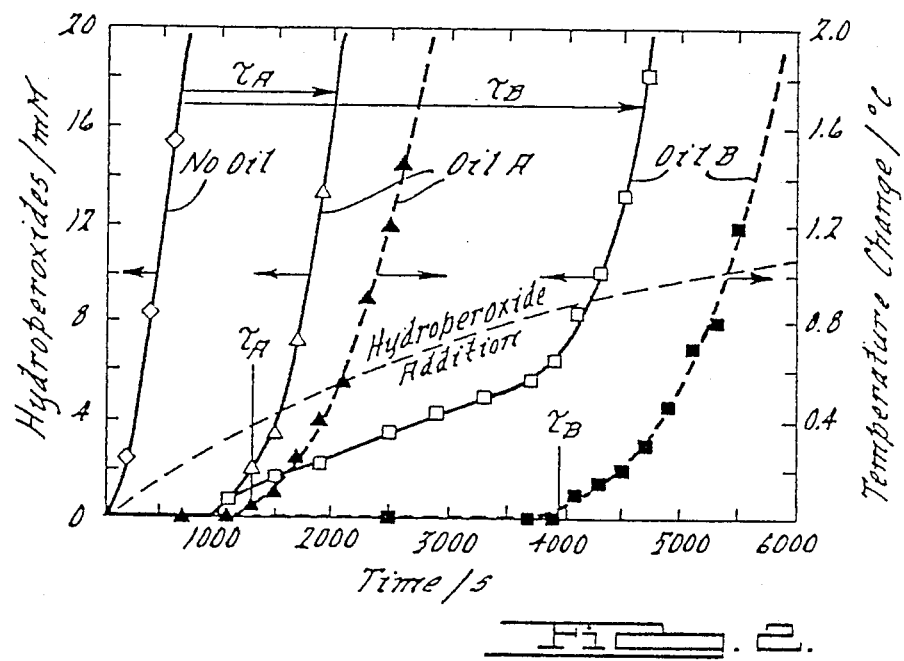
FIG. 2 is a graph illustrating changes in hydroperoxide concentration and temperature, as a function of time, during testing of two engine oils according to the method of this invention as described in Example 1. Determination of the length of the inhibition periods, $\tau$, which are a function of antioxidant capability, is shown.

Results of hydroperoxide analyses and temperature measurements for pure n-hexadecane (blank experiment), oil A, and oil B are plotted as functions of time in FIG. 2. From this data, the delays in oxidative breakdown (inhibition time), $\tau$, of oils A and B were determined as described in (c) above. Based on results of these determinations (Table 1) and the flow rate of peroxidic solution added, the relative antioxidant capabilities of tested oils were expressed as inhibition time per 1 mL of oil, AC $\tau$ (s/mL), or as moles of hydroperoxides needed per liter of oil to reach the oxidative breakdown, $AC_{OOH}$ (mole/L). Results of these determinations indicate that antioxidant capability of oil B is much greater than that of oil A.

TABLE 1

ANTIOXIDANT CAPABILITY OF ENGINE OILS

| ENGINE OIL | TEMP. [−OOH] | $\tau$ (s) | AVERAGE | $AC_\tau$ (s/mL) | $AC_{OOH}$ (mole/L) |
|---|---|---|---|---|---|
| Oil A | 1300 | 1360 | 1330 | 542 | 0.072 |
| Oil B | 3950 | 4000 | 3975 | 1646 | 0.222 |

EXAMPLE 2

Antioxidant Capability of Used Engine Oils

In this example, the antioxidant capabilities of used engine oils from unique service, oils C1 and C2, are compared to that of the corresponding new oil, oil C, using similar apparatus and procedures as those described in Example 1. The following were the modifications in the procedure: initial amount of n-hexadecane was 29 mL, added oil sample size was 1 mL, the rate of introduction of peroxidic solution was 1.67 µL/s, no samples of the reaction mixture were withdrawn, temperature measurements were used to determine the delay in oxidative breakdown, and values of $\tau$ were corrected for the delay observed with pure n-hexadecane (without adding oil).

Materials Assessed

Oil C—Mineral engine oil (10W40, SE).

Oil C1—Used engine oil sample obtained from a 5.0L engine in a Mark VII vehicle after 580 miles of unique service using oil C.

Oil C2—Similar used engine oil sample as oil C1, however, after 3013 miles of unique service.

Results

Figure 3:
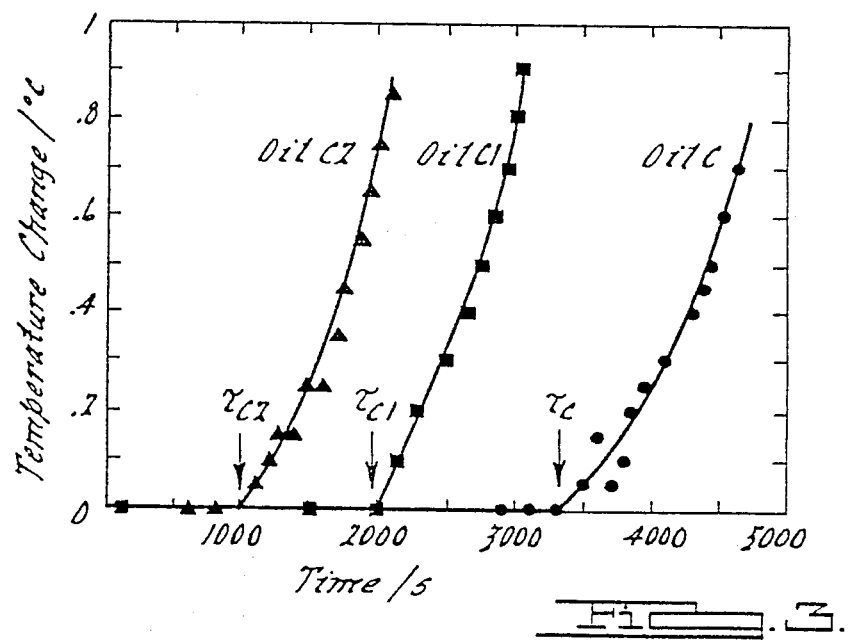
FIG. 3 is a graph depicting temperature changes and determination of inhibition periods for a fresh oil and the same oil after service as described in Example 2.

Results of temperature measurements from experiments with oils C, C1, and C2 are shown in FIG. 3. Corresponding inhibition times, $\tau$, and antioxidant capabilities, $AC\tau$ expressed as described in Example 1, are summarized in Table 2.

TABLE 2

ANTIOXIDANT CAPABILITY OF USED ENGINE OILS

| ENGINE OIL | MILES ON OIL | $\tau$ (s) | $AC_\tau$ (s/mL) | $AC_{OOH}$ (mole/L) |
|---|---|---|---|---|
| OIL C | 0 | 3320 | 3320 | 0.076 |
| OIL C1 | 580 | 1950 | 1950 | 0.044 |
| OIL C2 | 3013 | 1000 | 1000 | 0.023 |

EXAMPLE 3

Antioxidant Capability of Base Oils

In this example, antioxidant capabilities of two types of base oils, base oil A and base oil B, used in formulation of engine oils are compared using similar reagents, apparatus and procedures as those described in Example 1. The solution of peroxidic compounds was also prepared similarly, however, at the residence time of 418 s, consequently, [—OOH] of the solution was 15.0 mM. The following were the modifications in the procedure: initial amount of n-hexadecane was 30 mL and added base oil amounts were 10 mL.

Figure 4:
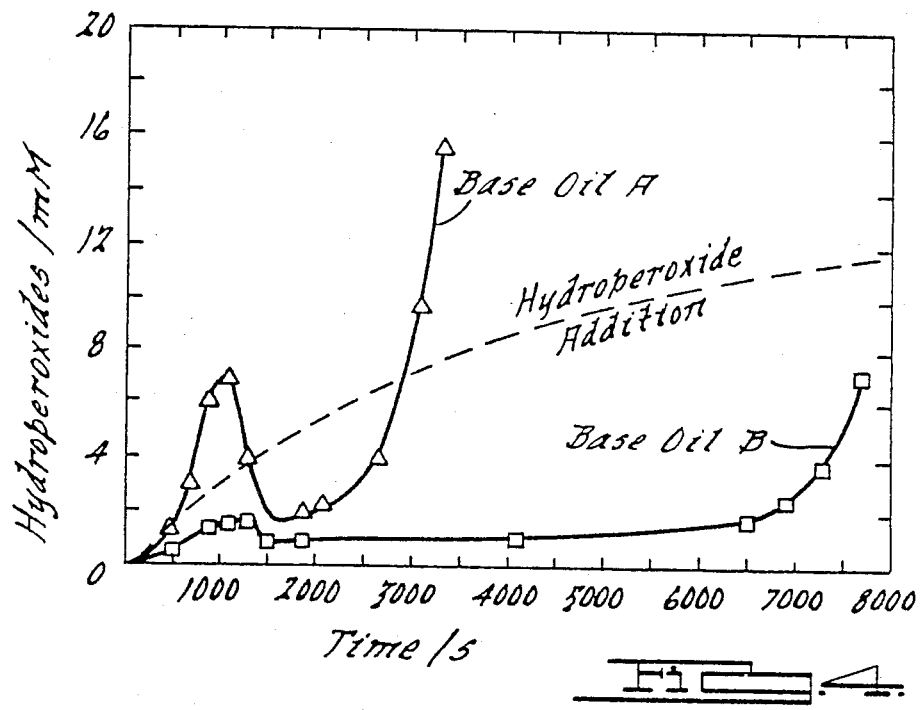
FIG. 4 is a graph showing changes in hydroperoxide concentration during testing of two base oils as described in Example 3.

Results:

Results obtained from hydroperoxide analyses of samples withdrawn from the reaction mixture are plotted in FIG. 4 as functions of reaction time. Inhibition times and corresponding antioxidant capabilities of the base oils are listed in Table 3. From these results it is obvious that said base oils do not only significantly differ in antioxidant capabilities but also exhibit different behavior during the test.

TABLE 3

ANTIOXIDANT CAPABILITY OF BASE OILS

| BASE OIL | $\tau$ (s) | $AC_\tau$ (s/mL) | $AC_{OOH}$ (mole/L) |
|---|---|---|---|
| Base Oil A | 2530 | 253 | 0.038 |
| Base Oil B | 7280 | 728 | 0.109 |

EXAMPLE 4

Antioxidant Capability of Additives

In this example, antioxidant capabilities of a peroxide decomposing antioxidant, nC$_8$ZDTP, radical trapping antioxidant, MPH, and their mixture have been determined using similar reagents, apparatus and procedures as those described in Example 1. The following were the modifications in the procedure: antioxidants were added as liquid (nC$_8$ZDTP) using a precision syringe or as solids (MPH) using a glass spatula into such amount of n-hexadecane that the initial volume of the reaction mixture was 40 mL.

Materials Assessed nC$_8$ZDTP—Zinc di-n-octyldithiophosphate.
MPH—2,6-di-tert-butyl-4-methylphenol.

Results

Figure 5:
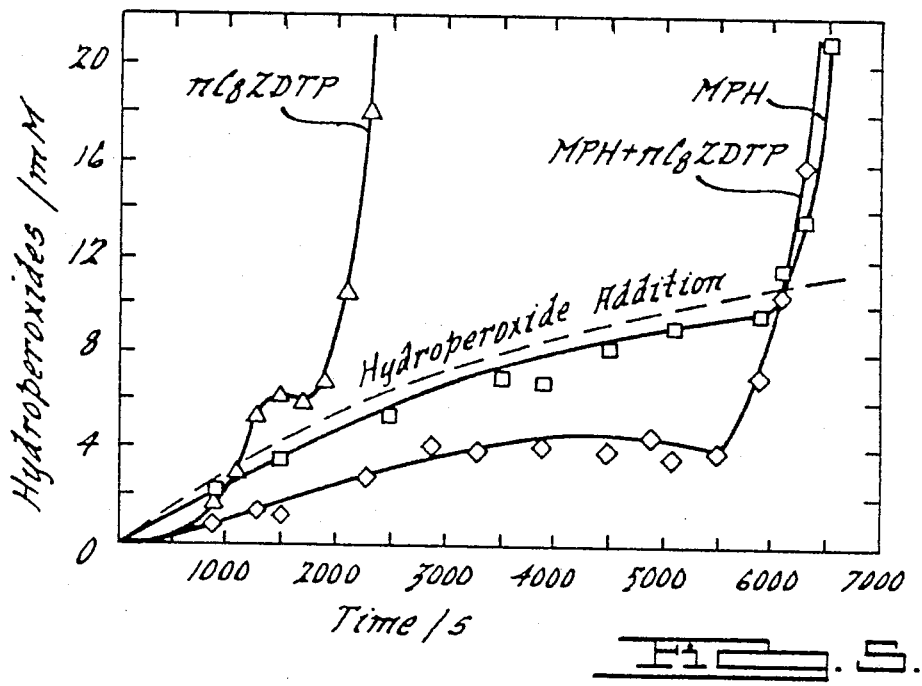
FIG. 5 is a graph showing changes in hydroperoxide concentration during testing of antioxidants as described in Example 4.

Results obtained from the hydroperoxide analyses of samples withdrawn from the reaction mixture are plotted in FIG. 5 as functions of reaction time. Inhibition times and corresponding antioxidant capabilities of the antioxidants evaluated are listed in Table 4.

TABLE 4

ANTIOXIDANT CAPABILITY OF ENGINE OIL ADDITIVES

| ANTIOXIDANT | INITIAL CONCENTRATION ($10^{-4}$ M) | $\tau$ (s) | $AC_\tau$ (s/mmole) | $AC_{OOH}$ (mole/mole) | $AC_{OOH}$ (mmole/g) |
|---|---|---|---|---|---|
| nC$_8$ZDTP | 10.4 | 1640 | 39,400 | 5.40 | 7.0 |
| MPH | 42.0 | 5790 | 34,500 | 4.72 | 21.4 |
| nC$_8$ZDTP + MPH | 10.6 + 42.6 | 5710 | 26,800 | 3.68 | 11.1 |

We claim:

1. A method for assessing the high temperature antioxidant capabilities of materials for both radical trapping and peroxide decomposing antioxidant species, which materials are selected from engine oils, base oils, and engine oil additives, under conditions simulating those encountered in an operating internal combustion engine, which method comprises:
   (a) oxidizing said materials in a reactor by means of an oxidizing gas comprising oxygen and at a temperature between about 100° C. and about 200° C., while concurrently and continuously introducing free radicals or materials capable of breaking down into free radicals into the reaction mixture,
   (b) monitoring the extent of the oxidation of said reaction mixture, and
   (c) determining the delay in the oxidative breakdown of said reaction mixture attributable to said antioxidant species present in said reaction mixture.

2. A method according to claim 1, wherein said materials to be assessed are employed in solution in an oxidizable solvent.

3. A method according to claim 2, wherein said solvent is selected from (i) n-hexadecane and (ii) pentaerythrityl tetraheptanoate.

4. A method according to claim 2, wherein, prior to oxidation of said reaction mixture, an oxidation catalyst is added into said materials to be assessed, employed in solution in an oxidizable solvent, to accelerate the oxidation.

5. A method according to claim 1, wherein, prior to oxidation of said reaction mixture, an oxidation catalyst is added into said materials to be assessed to accelerate the oxidation.

6. A method according to claim 1, wherein said oxidizing gas further comprises gases selected from inert gases and free radical gases.

7. A method according to claim 6, wherein said oxidizing gas is ambient air.

8. A method according to claim 1, wherein said free radicals are introduced into said reaction mixture as a gas comprising gaseous free radicals.

9. A method according to claim 8, wherein said gaseous free radicals are selected from gaseous free radical nitrogen oxides.

10. A method according to claim 8, wherein said gas comprising said gaseous free radicals is introduced into said reaction mixture with a stream of said oxidizing gas.

11. A method according to claim 8, wherein said source of said gaseous free radicals and said oxygen is the gaseous combustion product produced by combusting hydrocarbon fuels in the presence of oxygen.

12. A method according to claim 1, wherein said materials capable of breaking down into free radicals are employed in solution in a solvent.

13. A method according to claim 12, wherein said solvent is an oxidizable solvent.

14. A method according to claim 1, wherein said materials capable of breaking down into free radicals are selected from peroxidic compounds.

15. A method according to claim 14, wherein said peroxidic compounds are obtained by the oxidation of (i) n-hexadecane or (ii) pentaerythrityl tetraheptanoate.

16. A method according to claim 1, wherein step (b) comprises monitoring parameters selected from (i) measurement of the reaction temperature, (ii) determination of oxidation products, (iii) measurement of oxygen absorption, and (iv) measurement of physico-chemical properties.

17. A method according to claim 16, wherein the delay in the oxidative breakdown is determined from the change of said monitoring parameters.

18. A method for assessing the high temperature antioxidant capablity of materials for both radical trapping and peroxide decomposing antioxidant species, which materials are selected from engine oils, base oils, and engine oil additives under conditions simulating those encountered in an operating internal combustion engine, which method comprises:
   (a) oxidizing a solution of said materials in n-hexadecane in a reactor at a temperature between about 150° C. and about 190° C. and at atmospheric pressure by means of oxygen gas, while concurrently and continuously introducing preoxidized n-hexadecane containing hydroperoxides into the reaction mixture,
   (b) monitoring the extent of oxidation by monitoring parameters selected from temperature and/or said hydroperoxide concentration in said reaction mixture, and
   (c) determining the delay in oxidative breakdown of said reaction mixture from the increase of the temperature and/or from the delay of uninhibited formation of said hydroperoxides in said reaction mixture.

19. A method according to claim 18, wherein, prior to oxidation of said reaction mixture, an oxidation catalyst is added into said materials in said reactor to accelerate the oxidation.

* * * * *